United States Patent von Daehne

[11] 4,004,004
[45] Jan. 18, 1977

[54] FUSIDIC ACID DERIVATIVES

[75] Inventor: Welf von Daehne, Rungsted Kyst, Denmark

[73] Assignee: Leo Pharmaceutical Products Ltd. A/S, Ballerup, Denmark

[22] Filed: Aug. 12, 1975

[21] Appl. No.: 604,083

[30] Foreign Application Priority Data

Sept. 12, 1974 United Kingdom ............ 39891/74

[52] U.S. Cl. ............................ 424/238; 260/397.1
[51] Int. Cl.² ........................................ A61K 31/56
[58] Field of Search .................. 260/397.1; 424/238

[56] References Cited

UNITED STATES PATENTS 3,867,413  2/1975  Daehne et al. ................. 260/397.1

*Primary Examiner* — Elbert L. Roberts
*Attorney, Agent, or Firm* — Cushman, Darby & Cushman

[57] ABSTRACT

The present invention relates to a series of new fusidic acid derivatives and salts or easily hydrolysable esters thereof, to the preparation of these compounds and to pharmaceutical compositions containing the compounds. The new compounds have the general formula:

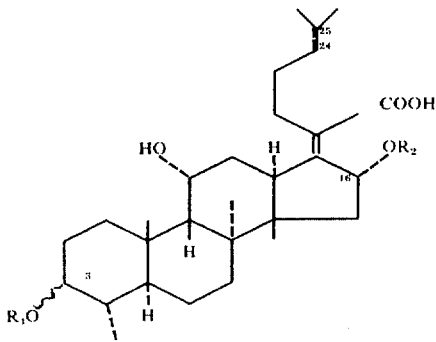

in which $R_1$ and $R_2$ stand for an alkanoyl, aralkanoyl or aroyl radical and $R_2$ also can be hydrogen; the dotted line between C-24 and C-25 indicates a double bond or a single bond, and the wavy line at C-3 indicates that $OR_1$ is either α-oriented or β-oriented. The compounds of the invention have a remarkable anti-inflammatory effect and cause a pronounced relief on patients suffering from arthritis.

The invention also concerns intermediates which in themselves to some extent have an anti-inflammatory activity.

10 Claims, No Drawings

FUSIDIC ACID DERIVATIVES

The present invention relates to a series of new fusidic acid derivatives and salts or easily hydrolysable esters thereof, to the preparation of these compounds and to pharmaceutical compositions containing the compounds. The new compounds have the general formula:

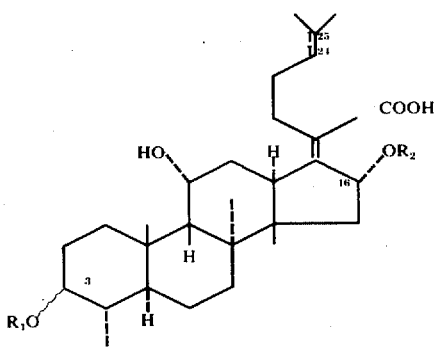

in which $R_1$ and $R_2$ stand for an alkanoyl, aralkanoyl or aroyl radical and $R_2$ also can be hydrogen; the dotted line between C-24 and C-25 indicates a double bond or a single bond, and the wavy line at C-3 indicates that $OR_1$ is either α-oriented or β-oriented. More particularly, $R_1$ and $R_2$ stand for a lower alkanoyl radical having from 2 to 8 carbon atoms such as the acetyl, propionyl, butyryl, valeryl, pivaloyl, caproyl, or caprylyl radicals, an aryl-lower alkanoyl radical, the aryl group of which being a mono- or bicyclic, carbocyclic radical, such as a phenyl or a naphthyl radical, and the alkanoyl radical having from 2 to 8 carbon atoms, and a mono- or bicyclic, carbocyclic aroyl radical, such as a benzoyl or naphthoyl radical. The above radicals may be further substituted with lower alkyl radicals, hydroxy groups or lower alkoxy groups or halogen atoms. The salts of the compounds are especially the pharmaceutically acceptable, non-toxic salts, such as alkali metal salts and alkaline earth metal salts, e.g. sodium, potassium, or calcium salts, or silver salts as well as salts with ammonia or suitable non-toxic amines, e.g. lower alkyl amines, for example triethylamine, hydroxy-lower alkylamines, for example 2-hydroxyethylamine, bis-(2-hydroxyethyl)-amine or tri-(2-hydroxyethyl)-amine, cycloalkylamines, for example dicyclohexylamine, or benzylamines for example N,N'-dibenzyl-ethylenediamine, and dibenzylamine.

The easily hydrolysable esters can e.g. be alkanoyloxyalkyl, aralkanoyloxyalkyl, aroyloxyalkyl esters, such as acetoxymethyl, pivaloyloxymethyl, benzoyloxymethyl esters, and the corresponding 1'-oxyethyl derivatives, or alkoxycarbonyloxyalkyl esters, such as methoxycarbonyloxymethyl, ethoxycarbonyloxymethyl and the corresponding 1'-oxyethyl derivatives, or phthalide esters, or dialkylaminoalkyl esters, such as diethylaminoethyl esters.

It has been found that the compounds of the invention have a remarkable anti-inflammatory effect and cause e.g. a pronounced relief on patients suffering from arthritis when administered daily in appropriate dosage units.

Arthritis is a widespread disease which in serious cases may make such inroads on the general health of a person as to interfere with his normal functioning.

As is well known arthritis is a disease of the joints, characterized among others by changes in the synovial fluid and the synovial membranes, and by atrophic and hypertrophic changes in the bones.

The symptoms are pain by moving and swelling in the joints. Pain is variable, some patients proceed to extreme deformity without severe pain, but normally pain is an important factor influencing the production of deformity as it hinders movement, and the joints are kept in the position of greatest ease.

Various secondary symptoms might also occur, especially in severe cases.

The ethiology of arthritis is still unknown, but many attempts have been made in order to relieve or cure the disease. Best known is the prolonged treatment with non-steroidal anti-inflammatory drugs such as salicylic acid, phenylbutazone or indomethacin, with gold preparations, such as Myocrisin, or with the corticosteroids. Unfortunately often severe side-effects may occur in the prolonged treatment with these drugs.

Recently, promising results in the treatment of rheumatoid arthritis were obtained with fusidic acid and have been described in the complete specification to our British Patent Application no. 43156/1973. The compounds of the invention have been found to be more effective than fusidic acid on comparison with the parent compound in both an experimental model of arthritis in the rabbit and in adjuvant induced arthritis in the rat. It may also be an advantage that the compounds of the invention are antibacterially inactive against a large number of gram-positive and gram-negative bacteria.

Also in the clinic the compounds of the invention have proved to be efficacious; for instance a group of patients with severe arthritis has been treated with the sodium salt of 3-0-acetyl-16-epideacetylfusidic acid in daily doses of from 1.5 to 3 g during several months. As judged after objective as well as subjective criteria a considerable improvement of the arthritic symptoms was obtained. The compounds were well tolerated, and the only side-effect observed was mild gastro-intestinal inconveniences in the beginning of the treatment.

The preferred route of administration in the treatment of arthritis according to the invention is the oral route of administration, but also the local or parenteral route of administration is valuable in some cases.

In the treatment of patients with the compounds of the invention there can simultaneously be administered other drugs, in particular other anti-inflammatory drugs, such as salicylic acid, phenylbutazone, indomethacin, or corticosteroids, or the new compounds can be administered in form of compounded formulations containing such drugs.

In the systemic treatment a daily dose is from 200 milligrams to 4000 milligrams, preferably from 500 to 2000 milligrams and administered as such or in the form of one of their non-toxic and pharmaceutically acceptable salts or one of their easily hydrolysable esters.

In the local treatment of affected joints a sparingly soluble active composition of the invention is appropriately given in the amount of from 50 to 500 mg in the form of suspensions.

The daily dose is appropriately given in dosage units from 1 to 4 times a day continuously for a period up to several months, depending on the condition of the patient and under direction of a medical practitioner.

An appropriate dosage unit for systemic treatment contains from 100 to 1000 milligrams, preferably from 100 to 500 milligrams in the form of tablets, capsules, or ampoules, or other forms usable for systemic administration may be applied such as aqueous or oily suspensions, containing from 20 to 250 mg per milliliter, preferably from 40 to 200 mg per milliliter.

For local treatment the dosage unit contains from 10–100 mg, as an injectable form of presentation.

The compositions for the purpose of the invention can either be worked up to pharmaceutical forms of presentation such as granulate, tablets, pills, dragees, and suppositories, or the composition can be filled in medical containers such as capsules, or so far as mixtures are concerned, they may be filled in bottles or tubes or similar containers. Pharmaceutical organic or inorganic, solid or liquid carriers suitable for enteral, parenteral or local administration can be used to make up the composition. Water, gelatine, lactose, starch, magnesium stearate, talc, vegetable and animal oils and fats, benzyl alcohol, gum, polyalkylene glycol, petroleum jelly, cocoa butter, lanolin or other known carriers for medicaments are all suitable as carriers, while stabilizing agents, wetting and emulsifying agents, salts for varying the osmotic pressure or buffers for securing an adequate pH-value of the composition can be used as auxiliary agents.

For granulates, tablets, capsules or dragees the pharmaceutical composition of the invention appropriately contains from 25 percent to 98 percent of the active substance of the invention, calculated as the free acid, and in oral suspensions the corresponding amount is appropriately from 2–25 percent.

For parenteral use the compounds are preferably given by intravenous infusion of an aqueous solution containing from 0.1 to 2 percent of the active ingredient, or the compound might be given by injection of the compounds in pharmaceutical compositions with from 1 to 20 percent active ingredient.

As mentioned above the compounds may be administered as free acids, or in the form of salts with pharmaceutically acceptable, non-toxic bases, or as easily hydrolysable esters. The preferred salts are for instance the easily water-soluble sodium salts or the diethanolamine salts, but other pharmaceutically acceptable and non-toxic salts may be used, for instance salts which are slightly soluble in water in order to obtain a particular and an appropriate rate of absorption.

It is also an object of the present invention to provide a method for the preparation of the compounds of formula I and salts thereof.

In one method the compounds of formula I can be prepared by acylating in a first step a compound of the formula II to form a compound of formula III:

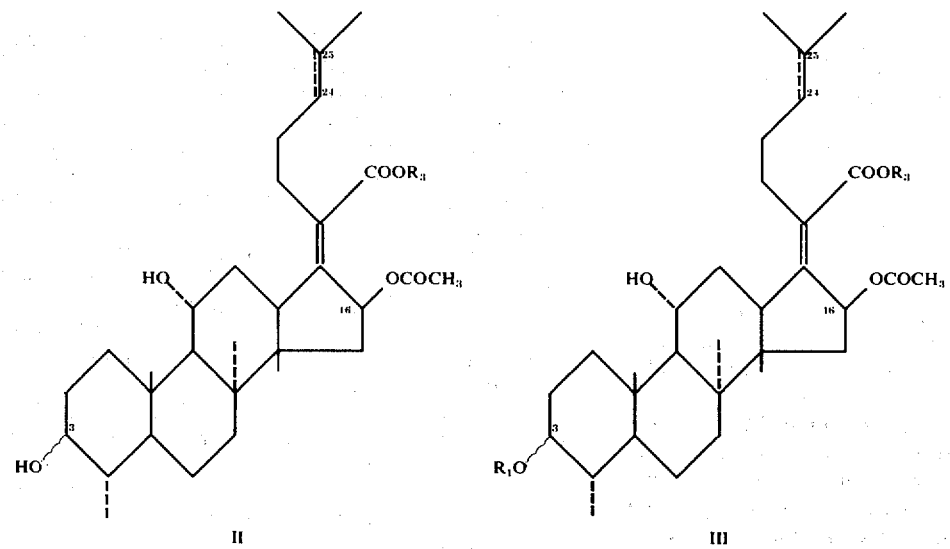

in which formulae $R_1$, the dotted line between C-24 and C-25, and the wavy line between C-3 and the oxygen substituent have the meaning as defined above, and $R_3$ stands for a hydrogen atom, an alkanoyloxymethyl or aroyloxymethyl radical, e.g. acetoxymethyl, pivaloyloxymethyl or benzoyloxymethyl, a cyanomethyl or an aralkyl radical such as a benzyl radical or a substituted benzyl radical, e.g. a p-nitrobenzyl or p-methoxybenzyl radical.

The acylation is performed in known manner by reacting a compound of formula II with an acid $R_1$—OH or a reactive derivative thereof, preferably an acid chloride or an acid anhydride.

When in the compounds of formula II $R_3$ is hydrogen it can be advantageous during the acetylation reaction to protect the carboxyl group as an easily hydrolysable ester group or an ester group which can be removed by hydrogenolysis. The esters are prepared by reacting a compound of formula II, in which $R_3$ stands for hydrogen, or a salt thereof, with an esterifying agent of the general formula $R_3X$, in which $R_3$ is defined as above, but is different from hydrogen, and X stands for a halogen atom, preferably chlorine or bromine, in an organic solvent, e.g. dimethylformamide, tetrahydrofuran or acetone, at room temperature or at slightly elevated temperature.

In the compounds of formula III ($R_3 \neq H$), the reconversion of the ester group into a carboxyl group can be effected by different procedures depending on what $R_3$ stands for. Catalytic hydrogenation, e.g. using palladium on carbon as a catalyst, will be preferred if $R_3$ stands for a cyanomethyl, a benzyl or a substituted benzyl radical, and reaction with a weak base in alcoholic or aqueous alcoholic solutions, preferably potassium carbonate in methanol, is performed if $R_3$ stands for an alkanoyloxymethyl or an aroyloxymethyl radical.

The compounds of formula III, with the exception of the compounds: 3-O-acetyl-fusidic acid, 3-O-acetyl-24,25-dihydrofusidic acid and the corresponding 3-epi compounds, are new and interesting intermediates, some of which also in themselves have anti-inflammatory activities. These compounds also constitute a part of this invention.

In the next step the free acids of formula III or salts thereof are selectively hydrolyzed at C-16 with inversion of the configuration. The hydrolysis is performed in water or a mixture of water and a suitable organic solvent such as methanol, ethanol or acetone under mild basic condition preferably at pH of about 7.5 to 9, e.g. with sodium or potassium bicarbonate, and at room temperature or at elevated temperature up to about 100° C, whereby the compounds of formula I, in which $R_2$ is hydrogen, are obtained.

The compounds of formula I in which $R_2$ is different from hydrogen, are thereafter obtained by reacting the compounds of formula I ($R_2$=H) with an acid $R_2$—OH ($R_2$ being different from H) or a reactive derivative thereof.

The easily hydrolysable esters of the compounds of formula I can be prepared in known manner by methods described in the literature.

When $R_1$ and $R_2$ in formula I represent the same radical these compounds can also be prepared in analogous manner to that described above by acylation of a fusidic acid derivative of the general formula IV:

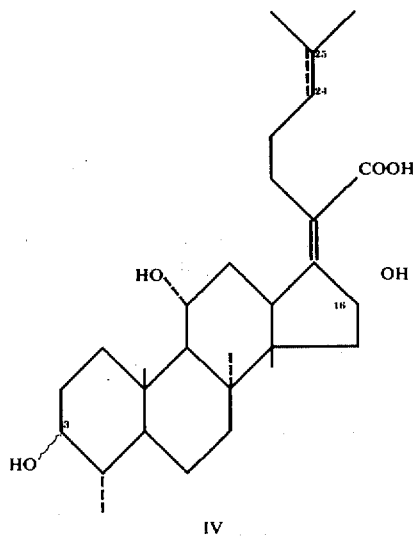

IV in which the dotted line between C-24 and C-25 and the wavy line between C-3 and the hydroxy group have the meaning as defined above.

The starting compounds of formula IV are known or can be prepared by conventional methods for preparing analogous known compounds.

As mentioned above for the acylation of the compounds of formula II ($R_3$ = H), it might also be an advantage to convert the carboxyl group of the compounds of formulae I ($R_2$ = H) and IV before the acylation reaction into easily hydrolysable esters or esters which can be removed by hydrogenolysis.

The 24,25-dihydro compounds of the invention can also be prepared by a catalytic hydrogenation of the corresponding unsaturated compounds of formula I in known manner.

In the following are given some examples on the preparation of intermediates which are illustrative but not limiting for the invention.

PREPARATION 1

Fusidic acid acetoxymethyl ester

To a solution of fusidic acid (25.84 g of the hemihydrate; 0.05 mol) in dimethylformamide (100 ml) was added triethylamine (7.1 ml; 0.05 mol) and, after stirring for 0.5 hour, chloromethyl acetate (9.0 ml; 0.1 mol). The mixture was stirred at room temperature overnight. After dilution with ethyl acetate (400 ml), water (100 ml) and triethylamine (3.55 ml; 0.025 mol) were added, and the mixture was shaken vigorously. The organic layer was separated, washed with water (4 × 100 ml), dried ($MgSO_4$), and evaporated in vacuo to yield 28 g of a yellowish gum. A solution of the crude material in ether (150 ml) was decolourized by treatment with charcoal (1.4 g) for 0.5 hour at reflux. After cooling, the charcoal was removed by filtration, and the filtrate was evaporated to dryness to give 23 g of a colourless foam. The residue was dissolved in diisopropyl ether (70 ml), and upon scratching a crystalline product precipitated. After standing overnight, petroleum ether (bp 50°–70° C.; 70 ml) was added to the mixture with stirring, the crystals were filtered off, washed with diisopropyl ether-petroleum ether 1:1, and dried to afford 18.04 g of fusidic acid acetoxymethyl ester, mp 95°–96° C. Concentration of the mother liquor gave another 3.08 g of the desired product, mp 94°–95° C. The analytical sample, mp 105°–106° C, was obtained by two recrystallizations from diisopropyl ether.

Found: C 69.27, H 8.91%

$C_{34}H_{52}O_8$ requires C 69.12, H 9.21%.

PREPARATIONS 2–5

Additional fusidic acid esters

By following the procedure of Preparation 1 but substituting the esterifying reagents shown in table I for the chloromethyl acetate, the fusidic acid esters indicated in table I were obtained.

Table I

[Structure: steroid skeleton with COOR, OCOCH₃, HO, HO substituents]

| Prep. | Esterifying agent | Resulting compounds R | Mp (° C) |
|---|---|---|---|
| 2 | chloromethyl pivalate | $CH_2OCOC(CH_3)_3$ | amorphous |
| 3 | chloromethyl benzoate | $CH_2OCOC_6H_5$ | amorphous |
| 4 | chloroacetonitrile | $CH_2CN$ | 125–126 |
| 5 | benzyl bromide | $CH_2C_6H_5$ | amorphous |

PREPARATION 6

3-Epifusidic acid acetoyxmethyl ester

By substituting 3-epifusidic acid for the fusidic acid in the procedure of Preparation 1, 3-epifusidic acid acetoxymethyl ester, mp 184°–186° C, was obtained.

Found: C 69.24, H 8.91%

$C_{34}H_{52}O_8$ requires C 69.36, H 8.90%.

PREPARATION 7

3-Epi-24,25-dihydrofusidic acid cyanomethyl ester

Following the procedure described in Preparation 1, but substituting 3-epi-24,25-dihydrofusidic acid for the fusidic acid and chloroacetonitrile for the chloromethyl acetate, 3-epi-24,25-dihydrofusidic acid cyanomethyl ester, mp 174°–176° C, was obtained.

Found: C 70.96, H 9.21, N 2.57%

$C_{33}H_{51}NO_6$ requires C 71.06, H 9.22, N 2.51%.

PREPARATION 8

16-Epideacetylfusidic acid benzyl ester

16-Epideacetylfusidic acid (9.5 g) was dissolved in methanol (50 ml) and converted into its sodium salt by titration with 5 N sodium hydroxide using phenolphthalein as indicator. After evaporation to dryness in vacuo, the resulting amorphous sodium salt was dissolved in N,N-dimethylformamide (50 ml), benzyl bromide (4.26 g) was added, and the mixture was stirred at room temperature for 16 hours. Water (100 ml) was added, and the mixture was extracted with ether (2 × 100 ml). The combined organic extracts were washed with water (4 × 50 ml), dried, and evaporated in vacuo. The residual gum was dissolved in methanol (50 ml), water (25 ml) was added dropwise with stirring, and upon scratching a crystalline product precipitated. The crystals were collected, washed with methanol-water 2:1, and dried to give 9.72 g of 16-epideacetylfusidic acid benzyl ester, mp 94°–96° C.

PREPARATIONS 9–12

Additional 16-epideacetylfusidic acid esters

Following the procedure described in Preparation 8, but substituting the esterifying agents shown in table II for the benzyl bromide, the 16-epideacetylfusidic acid esters listed in table II were obtained.

Table II

[Structure: steroid skeleton with COOR, HO, OH, HO substituents]

| Prep. | Esterifying agent | Resulting compounds R | Mp (° C) |
|---|---|---|---|
| 9 | chloromethyl acetate | $CH_2OCOCH_3$ | amorphous |
| 10 | chloromethyl pivalate | $CH_2OCOC(CH_3)_3$ | amorphous |
| 11 | chloromethyl benzoate | $CH_2OCOC_6H_5$ | amorphous |
| 12 | chloroacetonitrile | $CH_2CN$ | amorphous |

The invention will now be illustrated by the following non-limiting Examples from which the details of the embodiment will be apparent.

EXAMPLE 1

3-O-Acetyl-16-epideacetylfusidic acid

To a solution of sodium bicarbonate (25.23 g) in water (2 l) was added 3-O-acetylfusidic acid (57.68 g of the monohydrate), and, after stirring for 0.5 hr at room temperature, the mixture was heated to 100° C on an electric heating bath. The almost clear solution thus obtained was refluxed for 1 hr, and during this time precipitation of a crystalline by-product occurred.

After removal of this by filtration and washing, ethyl acetate (600 ml) was added to the combined filtrate and washings, and the apparent pH-value of the mixture was adjusted to 2 by addition of 4 N hydrochloric acid with stirring. After separation of the organic phase, the aqueous layer was reextracted with ethyl acetate (400 ml). The combined organic extracts were washed with water until neutral, dried, and the solution was concentrated to about 100–120 ml at reduced pressure. To the concentrate was added petroleum ether (bp 50°–70° C; 300 ml) with stirring which furnished precipitation of a crystalline product. After being kept at room temperature overnight, the crystals were filtered off, washed with ethyl acetate-petroleum ether 1:4 and dried to yield 20.32 g of 3-O-acetyl-16-epideacetylfusidic acid, mp 173.5°–175° C. The mother liquor was evaporated to dryness, the resulting amorphous residue (18.6 g) was dissolved in ethyl acetate (40 ml), and petroleum ether (160 ml) was added. Upon scratching a second crop of crystalline product was obtained, which was filtered off, washed, and dried to give 0.96 g of the desired compound, mp 171°–173° C. Two recrystallizations from ethyl acetate-petroleum ether afforded the analytically pure compound, mp 177°–178° C; $[\alpha]_D^{20} -71°$ (c 1, $CHCl_3$).

Found: C 71.96; H 9.33%. $C_{31}H_{48}O_6$ (516.73) requires: C 72.06; H 9.36%.

EXAMPLE 2

3-O-Acetyl-16-epiacetyl-24,25-dihydrofusidic acid

Following the procedure described in Example 1, but substituting 3-O-acetyl-24,25-dihydrofusidic acid (57.88 g of the monohydrate) for 3-O-acetylfusidic acid, 26.58 g of 3-O-acetyl-16-epiacetyl-24,25-dihydrofusidic acid, mp 179°–180° C, was obtained. Two recrystallizations from ethyl acetate-petroleum ether yielded the analytically pure compound, mp 183°–184° C; $[\alpha]_D^{20} -60°$ (c 1, $CHCl_3$).

Found: C 71.69; H 9.63%. $C_{31}H_{50}O_6$ (518.74) requires: C 71.78; H 9.72%.

EXAMPLE 3

3-O-Propionyl-16-epiacetylfusidic acid

A. 3-O-Propionylfusidic acid

Fusidic acid (100 g of the hemihydrate) was dissolved in a mixture of pyridine (75 ml) and propionic anhydride (75 ml). After standing for 16 hrs at room temperature, the mixture was poured into ice-water (about 1.2 l) with stirring to give precipitation of an oily product. The aqueous layer was removed by decantation, and the oily residue was washed by decantation with water (3 × 400 ml). To the residual gum was added methanol (250 ml), and on stirring for 0.5 hr at 40° C a crystalline product was formed. After cooling to room temperature, the crystals were collected, washed with methanol-water 4:1, and dried to afford 87.3 g of 3-O-propionylfusidic acid, mp 171°–173° C. Addition of water (about 40 ml) to the combined filtrate and washings afforded a second crop (21.1 g) of the desired product, mp 170°–172° C. Two recrystallizations from methanol-water gave the analytically pure compound, mp 175°–176° C.

Found: C 67.05; H 9.14; $H_2O$ 5.37%. $C_{34}H_{52}O_7$, 2 $H_2O$ (608.82) requires: C 67.07; H 9.27; $H_2O$ 5.92%.

B. 3-O-Propionyl-16-epiacetylfusidic acid

Following the procedure described in Example 1, but substituting 3-O-propionylfusidic acid for the 3-O-acetylfusidic acid, 3-O-propionyl-16-epiacetylfusidic acid, mp 171°–173° C, was obtained. Two recrystallizations from ethyl acetate-petroleum ether afforded the analytically pure material, mp 177°–178° C.

Found: C 72.24; H 9.40%. $C_{32}H_{50}O_6$ (530.75) requires: C 72.41; H 9.50%.

EXAMPLE 4

3-O-Butyryl-16-epiacetylfusidic acid

A. 3-O-Butyrylfusidic acid

By following the procedure of Example 3 A, but substituting butyric anhydride for the propionic anhydride, 3-O-butyrylfusidic acid, mp 160°–161° C, was obtained.

Found: C 71.67; H 9.30%. $C_{35}H_{54}O_7$ (586.82) requires: C 71.64; H 9.28%.

B. 3-O-Butyryl-16-epiacetylfusidic acid

By substituting 3-O-butyrylfusidic acid for the 3-O-acetylfusidic acid in the procedure of Example 1, 3-O-butyryl-16-epiacetylfusidic acid, mp 145°–146° C, was obtained.

Found: C 72.88; H 9.45%. $C_{33}H_{52}O_6$ (544.78) requires: C 72.55; H 9.45%.

EXAMPLE 5

3-O-Benzoyl-16-epiacetylfusidic acid

A. 3-O-Benzoylfusidic acid acetoxymethyl ester

To a stirred solution of fusidic acid acetoxymethyl ester (35.3 g; 60 mmol) in a mixture of methylene chloride (60 ml) and pyridine (40 ml) was added at 0° C a solution of benzoyl chloride (6.9 ml; 90 mmol) in methylene chloride (20 ml). After stirring at 0° C for 30 minutes, the cooling bath was removed, and the mixture stirred at room temperature overnight. Ice-water (400 ml) was added, and the mixture was extracted with ether (2 × 200 ml). The combined organic extracts were washed with diluted hydrochloric acid (to remove pyridine), water, 0.5 N aqueous sodium bicarbonate, and water, dried, and evaporated in vacuo. The residual oil crystallized from ether-petroleum ether to yield 37.8 g of 3-benzoylfusidic acid acetoxymethyl ester, mp 156°–158° C. Recrystallization from the same solvents gave the analytical sample, mp 158°–160° C.

Found: C 70.89, H 7.99%, $C_{41}H_{56}O_9$ (692.90) requires: C 71.07, H 8.15%.

B. 3-O-Benzoylfusidic acid

To a solution of 3-O-benzoylfusidic acid acetoxymethyl ester (32.4 g; 50 mmol) in methanol (200 ml) was added potassium carbonate (17.3 g; 125 mmol), and the mixture was stirred at room temperature for 30 minutes. After removal of the major part of the solvent in vacuo, ethyl acetate (200 ml) and water (200 ml) were added to the residue, and the stirred mixture was acidified with diluted hydrochloric acid. Thr organic phase was separated, the aqueous phase was reextracted with ethyl acetate (100 ml) and the combined organic extracts were washed with water, dried, and evaporated in vacuo. The resulting amorphous residue was dissolved in methylene chloride (100 ml), diisopropyl ether (200 ml) was added, and, after removal of the methylene chloride by distillation, a crystalline product precipitated. The crystals were filtered off, washed with diisopropyl ether, and dried to afford 27.5 g of 3-O-benzoylfusidic acid, mp 184°–186° C. Recrystallization from methylene chloride diisopropyl ether gave the analytically pure compound, mp 188°–189° C.

Found: C 73.23, H 8.37%, $C_{38}H_{52}O_7$ (620.83) requires: C 73.51, H 8.44%.

C. 3-O-Benzoyl-16-epiacetylfusidic acid

By substituting 3-O-benzoylfusidic acid for the 3-O-acetylfusidic acid in the procedure of Example 1, 3-O-benzoyl-16-epiacetylfusidic acid, mp 119°–122° C was obtained.

EXAMPLE 6

3-O-Pivaloyl-16-epiacetylfusidic acid

A. 3-O-Pivaloylfusidic acid acetoxymethyl ester

Following the procedure described in Example 5 A, but substituting pivaloyl chloride for the benzoyl chloride, 3-O-pivaloylfusidic acid acetoxymethyl ester, mp 150°–152° C, was obtained.

Found: C 69.48, H 8.94%, $C_{39}H_{60}O_9$ (672.91) requires: C 69.61, H 8.99%.

B. 3-O-Pivaloylfusidic acid

By substituting 3-O-pivaloylfusidic acid acetoxymethyl ester for the 3-O-benzoylfusidic acid acetoxymethyl ester in the procedure of Example 5 B, 3-O-pivaloylfusidic acid, mp 179°–181° C, was obtained.

Found: C 71.55, H 9.56%, $C_{36}H_{56}O_7$ (600.84) requires: C 71.96, H 9.40%.

C. 3-O-Pivaloyl-16-epideacetylfusidic acid

Following the procedure described in Example 1, but substituting 3-O-pivaloylfusidic acid for the 3-O-acetylfusidic acid, 3-O-pivaloyl-16-epideacetylfusidic acid, mp 172°–174° C, was obtained.

Found: C 72.83, H 9.56%, $C_{34}H_{54}O_6$ (558.81) requires: C 73.08, H 9.74%.

EXAMPLE 7

3-O-Acetyl-16-epi-24,25-dihydrofusidic acid

16-Epideacetyl-24,25-dihydrofusidic acid (30 g) was dissolved in a mixture of pyridine (60 ml) and acetic anhydride (60 ml). After standing for 3 hrs at room temperature, the mixture was poured into ice-water (about 1 l), and the oily precipitate which formed was extracted with ethyl acetate (2 × 250 ml). The combined organic phases were washed with diluted hydrochloric acid (to remove pyridine), followed by water, and dried. A colourless product began to crystallize, and the mixture was kept in the refrigerator overnight. The crystals were filtered off, washed with ethyl acetate, and dried to yield 10.82 g of 3-O-acetyl-16-epideacetyl-24,25-dihydrofusidic acid lactone, formed as a by-product.

The ethyl acetate solution of the filtrate was extracted with 0.5 N sodium hydroxide (2 × 100 ml) and washed with water until neutral. To the combined aqueous phase was added ethyl acetate (200 ml), and the apparent pH-value of the mixture was adjusted to 2 by addition of 4 N hydrochloric acid with stirring. The organic layer was separated, washed with water, dried, and evaporated in vacuo to give 17.6 g of an amorphous product. The residue was dissolved in methanol (150 ml), and on addition of water (50 ml) with stirring a crystalline compound precipitated. The crystals were filtered off, washed with methanol-water 3:1, and dried to afford 13.62 g of 3-O-acetyl-16-epi-24,25-dihydrofusidic acid, mp. 171°–172° C. Recrystallization from methanol-water gave the analytical sample, mp. 173°–174° C.

Found: C 69.35; H 9.31%. $C_{33}H_{52}O_7$, 0.5 $H_2O$ (569.79) requires: C 69.56; H 9.38%.

EXAMPLE 8

3-O-Acetyl-16-deacetoxy-16α-phenylacetoxy-24,25-dihydrofusidic acid

A. 3-O-Acetyl-16-epideacetylfusidic acid benzyl ester

To a stirred solution of 3-O-acetyl-16-epideacetylfusidic acid (10.33 g; 20 mmol) and triethylamine (4.2 ml; 30 mmol) in N,N-dimethylformamide (50 ml) was added benzyl bromide (3.57 ml; 30 mmol). After a few minutes, crystalline triethylammonium bromide began to precipitate, and the mixture was stirred at room temperature for 16 hours. The suspension was diluted with methanol (50 ml), and a clear solution was obtained. Water (50 ml) was added dropwise to the stirred solution, and upon scratching a crystalline product precipitated. After stirring for a further 30 minutes, the crystals were collected, washed with methanol-water 1:1 (3 × 10 ml), and dried to afford 9.98 g of 3-O-acetyl-16-epideacetylfusidic acid benzyl ester, mp 108°–109° C.

B. 3-O-Acetyl-16-deacetoxy-16α-phenylacetoxyfusidic acid benzyl ester

A solution of phenylacetyl chloride (3.0 ml; 22.5 mmol) in methylene chloride (10 ml) was added dropwise at 5° C to a stirred solution of 3-O-acetyl-16-epideacetylfusidic acid benzyl ester (9.11 g; 15 mmol) in a mixture of methylene chloride (15 ml) and pyridine (10 ml). After the addition was finished, the cooling bath was removed and the mixture stirred at room temperature overnight. Ice-water (about 100 ml) was added, and the mixture was extracted with ether (2 × 50 ml). The combined organic extracts were washed with diluted hydrochloric acid, water, 0.5 N sodium bicarbonate, and water, dried, and evaporated in vacuo. The residual yellow oil was decolourized by treatment with charcoal (1 g) in refluxing ether (100 ml) for 2 hours. The charcoal was removed by filtration, and the filtrate evaporated to dryness. The amorphous residue thus obtained crystallized from methanol to afford 8.22 g of 3-O-acetyl-16-deacetoxy-16α-phenylacetoxyfusidic acid benzyl ester, mp 133°–137° C. The recrystallizations from methanol gave the analytically pure compound, mp 140°–141° C.

Found: C 76.21, H 8.33%, $C_{46}H_{60}O_7$ (724.99) requires: C 76.21, H 8.34%.

C. 3-O-Acetyl-16-deacetoxy-16α-phenylacetoxy-24,25-dihydrofusidic acid

To a solution of 3-O-acetyl-16-deacetoxy-16α-phenylacetoxyfusidic acid benzyl ester (3.63 g; 5 mmol) in dioxane (50 ml) was added 10% palladium on carbon catalyst, and the mixture was shaken in a hydrogen atmosphere for 40 minutes. The catalyst was filtered off, washed with dioxane, and the combined filtrate and washing were evaporated in vacuo. The amorphous residue thus obtained crystallized from ether-petroleum ether to yield 2.54 g of 3-O-acetyl-16-deacetoxy-16α-phenylacetoxy-24,25-dihydrofusidic acid, mp 163°–164° C.

EXAMPLE 9

Sodium salt of 3-O-acetyl-16-epideacetylfusidic acid

A crystalline sodium salt of the acid of Example 1 was obtained on titration of a solution of 3-O-acetyl-16-epideacetylfusidic acid (20.67 g) in methanol (80 ml) with 2 N methanolic sodium hydroxide using phenolphthalein as indicator, dilution with 2-butanone (400 ml), and concentration of the resulting mixture to about 200 ml at reduced pressure. After standing for 30 minutes, the crystals were filtered off, washed with 2-butanone followed by ether, and dried to afford 21.2 g of the sodium salt of 3-O-acetyl-16-epideacetylfusidic acid, mp 183°–185° C. Recrystallization from methanol-2-butanone gave the analytically pure compound, mp 184°–186° C.

Found: C 68.10, H 8.91, $H_2O$ 1.67% $C_{31}H_{47}O_6Na$, 0.5 $H_2O$ requires: C 67.98, H 8.83, $H_2O$ 1.65%.

EXAMPLE 10

Sodium salt of 3-O-propionyl-16-epideacetylfusidic acid

A crystalline sodium salt of the acid of Example 3 was prepared by titration of a solution 3-O-propionyl-16-epideacetylfusidic acid (21.23 g) in methanol (100 ml) with 2 N methanolic sodium hydroxide against phenolphthalein, addition of diisopropyl ether (400 ml), and concentration of the resulting mixture to about 150 ml at reduced pressure. After being kept in the refrigerator overnight, the crystals were collected, washed with diisopropyl ether, and dried to afford 20.55 g of the sodium salt of 3-O-propionyl-16-epideacetylfusidic acid mp 179°–182° C. Recrystallization from methanol-diisopropyl ether gave the analytical sample mp 181°–184° C.

Found: C 67.67, H 9.32% $C_{32}H_{49}O_6$ Na, $H_2O$ requires: C 67.34, H 9.01%.

EXAMPLE 11

Sodium salt of 3-O-acetyl-16-epi-24,25-dihydrofusidic acid

A crystalline sodium salt of the acid of Example 7 was obtained on titrating a solution of 3-O-acetyl-16-epi-24,25-dihydrofusidic acid (11.22 g) in methanol (75 ml) with 2 N methanolic sodium hydroxide using phenolphthalein as indicator, removal of the solvent in vacuo, and dissolution of the resulting amorphous product in acetone (100 ml). The crystals were filtered off, washed with acetone, and dried to yield 10.86 g of the sodium salt of 3-O-acetyl-16-epi-24,25-dihydrofusidic acid mp 177°–179° C.

Found: C 65.67, H 8.73, $H_2O$ 3.49% $C_{33}H_{51}O_7Na$, $H_2O$ requires: C 65.97, H 8.89, $H_2O$ 3.00%.

EXAMPLE 12

3-Epi-O-acetyl-16-epideacetyl-24,25-dihydrofusidic acid

By following the procedure described in Example 1 but substituting 3-epi-O-acetyl-24,25-dihydrofusidic acid for the 3-O-acetylfusidic acid, 3-epi-O-acetyl-16-epideacetyl-24,25-dihydrofusidic acid, mp 122°–125° C was obtained.

Found: C 69.08, H 9.95% $C_{31}H_{50}O_6$, $H_2O$ requires: C 69.37, H 9.77%.

EXAMPLE 13

3-O-Acetyl-16-epideacetylfusidic acid benzoyloxymethyl ester

To a solution of 3-O-acetyl-16-epideacetylfusidic acid sodium salt (5.48 g; 10 mmol of the hemihydrate) in N,N-dimethylformamide (50 ml) was added chloromethyl benzoate (1.59 ml; 11 mmol), and the mixture was stirred at room temperature for 16 hours. After dilution with ether (200 ml), the mixture was washed with water (4 × 50 ml, 2 × 25 ml), dried, and evaporated in vacuo to afford 6.4 g of the desired compound as a gum. Purification by dry column chromatography on silica gel (solvent system: petroleum ether - ethyl acetate 7:3) gave pure 3-O-acetyl-16-epideacetylfusidic acid benzoyloxymethyl ester as a colourless, amorphous product.

The nmr spectrum ($CD_3Cl$) shows signals at $\delta$ = 0.76(s, 3H; $CH_3$-18), 0.93(d, J=6, 3H; $CH_3$-30), 0.97(s, 3H; $CH_3$-19), 1.48(s, 3H; $CH_3$-32), 1.54 and 1.65(2 bs, 6H; $CH_3$-26 and $CH_3$-27), 2.07(s, 3H; $CH_3CO$ at C-3), 3.35(m, 1H; $CH$-13), 4.33(m, 1H; $CH$-11), 4.81(m, 1H; $CH$-16), 4.96(m, 1H; $CH$-3), 5.10(m, 1H; $CH$-24), 6.05 and 6.13(2d, J=5, 2H; O-$CH_2$-O), 7.25–7.67(m, 3H; arom. $CH$), and 7.92–8.20(m, 2H; arom. $CH$)ppm. Tetramethylsilane was used as internal reference.

EXAMPLES 14–19

Additional esters of 3-O-acetyl-16-epideacetylfusidic acid

By substituting the esterifying agents indicated in table III for the chloromethyl benzoate in the procedure of Example 13, the 3-O-acetyl-16-epideacetylfusidic acid esters listed in table III were obtained.

Table III

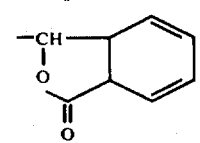

| Example | Esterifying agent | Resulting compounds R |
|---|---|---|
| 15 | chloromethyl acetate | $CH_2OCOCH_3$ |
| 16 | chloromethyl pivalate | $CH_2OCOC(CH_3)_3$ |
| 17 | 1-chloroethyl ethyl carbonate | —CHOCOOCH$_2$CH$_3$<br>    \|<br>    CH$_3$ |
| 18 | bromo phthalide | (phthalidyl structure) |

Table III-continued

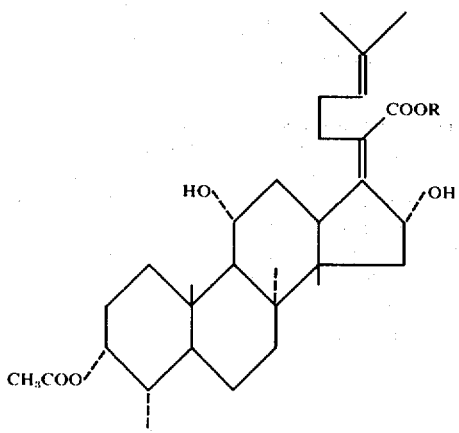

| Example | Esterifying agent | Resulting compounds R |
|---|---|---|
| 19 | N,N-diethylaminoethyl chloride | $CH_2CH_2N(C_2H_5)_2$ |

EXAMPLE 20

| Preparation of tablets | |
|---|---|
| Compound of Example 9 | 200 g |
| Avicel PH 101 | 100 g |
| STA-Rx 1500 | 100 g |
| Magnesiumstearate | 10 g |

The sodium salt of 3-O-acetyl-16-epideacetylfusidic acid, Avicel and STA-Rx are mixed together, sieved through a 0.7 mm sieve and thereafter mixed with the magnesiumstearate. The mixture is pressed into tablets each of 410 mg.

EXAMPLE 21

| Preparation of suspension | |
|---|---|
| Compound of Example 1 | 5.00 g |
| Citric acid | 0.45 g |
| Sodium monohydrogenphosphate | 0.70 g |
| Sucrose | 25.00 g |
| Tween 80 | 0.05 g |
| Potassium sorbate | 0.20 g |
| Carboxymethylcellulose-Na | 0.50 g |
| Purified water | qs to 100 ml suspension |

The crystals are micronized and suspended in a solution of the citric acid, the sodium monohydrogenphosphate, the sucrose, the potassium sorbate and the Tween 80 in 50 ml water, if necessary under slight warming. The carboxymethylcellulose-Na is dissolved in 20 ml of boiling water. After cooling, it is added to the other ingredients. The suspension is homogenized in a blender and finally purified water is added to a total volume of 100 ml.

Having thus described my invention what I claim as new and desire to secure by Letters Patent is:

1. A pharmaceutical composition in dosage unit form for the treatment of patients suffering from arthritis, which comprises as therapeutical ingredient at least one compound of the formula:

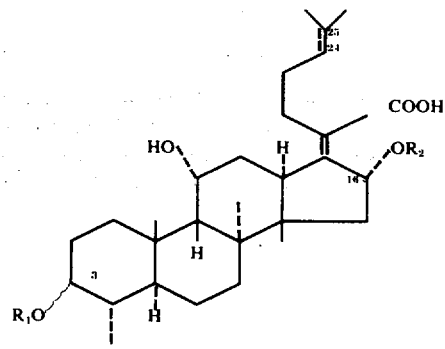

in which $R_1$ and $R_2$ stand for a lower alkanoyl radical having from 2 to 8 carbon atoms, a mono- or bicyclic, carbocyclic aryl-lower alkanoyl radical, or a mono- or bicyclic, carbocyclic aroyl radical; and $R_2$ also stands for hydrogen; the dotted line between C-24 and C-25 indicates a double bond or a single bond; and the wavy line at C-3 indicates that $OR_1$ is α- or β-oriented; and pharmaceutically acceptable, non-toxic salts or easily hydrolyzable esters thereof, said compound being admixed with an atoxic, pharmaceutically acceptable carrier, and the dosage unit being between 100 to 1000 mg calculated as the free acid of the therapeutically active compound.

2. A composition as claimed in claim 1 wherein the dosage unit is in the form of tablets.

3. A composition as claimed in claim 1 wherein the dosage unit is in the form of capsules.

4. A composition as claimed in claim 1 wherein the dosage unit is in the form of pills.

5. A composition as claimed in claim 1 wherein the dosage unit is in the injectable form of preparation and contains from 50 to 500 mg, calculated as the free acid, of the therapeutically active compound.

6. A composition as claimed in claim 1 wherein the dosage unit is a suspension for oral use and containing the therapautically active compound in an amount of from 2 to 25 percent.

7. A composition according to claim 1 in which the active ingredient is 3-O-acetyl-16-epideacetylfusidic acid or a pharmaceutically acceptable, non-toxic salt or easily hydrolyzable ester thereof.

8. A method of treating acute or chronic arthritis which comprises administering into the body an effective amount of a compound of the formula:

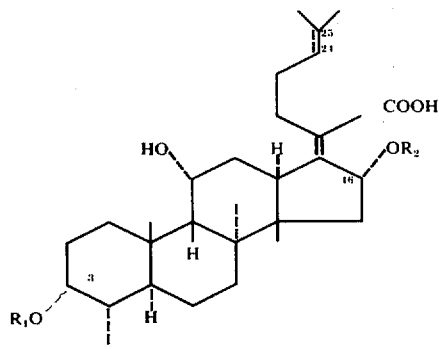

in which $R_1$ and $R_2$ stand for a lower alkanoyl radical having from 2 to 8 carbon atoms, a mono- or bicyclic, carbocyclic aryl-lower alkanoyl radical, or a mono- or bicyclic, carbocyclic aroyl radical; and $R_2$ also stands for hydrogen; the dotted line between C-24 and C-25 indicates a double bond or a single bond; and the wavy line at C-3 indicates that $OR_1$ is $\alpha$- or $\beta$-oriented; and pharmaceutically acceptable, non-toxic salts or easily hydrolyzable esters thereof.

9. A method according to claim 8 in which the therapeutically active compound is administered by the oral route, in amounts from 200 to 4000 mg per day, preferably from 500 to 2000 mg per day.

10. A pharmaceutical composition in dosage unit form for the treatment of arthritis comprising an effective amount of a compound of the formula:

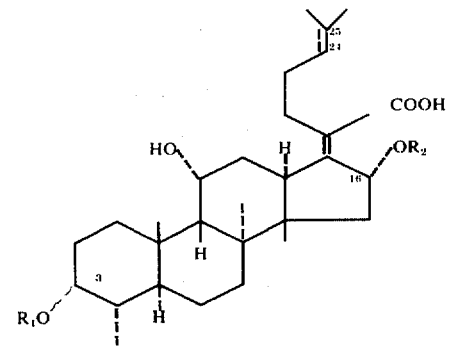

in which $R_1$ and $R_2$ stand for a lower alkanoyl radical having from 2 to 8 carbon atoms, a mono- or bicyclic, carbocyclic aryl-lower alkanoyl radical, or a mono- or bicyclic, carbocyclic aroyl radical; and $R_2$ also stands for hydrogen; the dotted line between C-24 and C-25 indicates a double bond or a single bond; and the wavy line at C-3 indicates that $OR_1$ is $\alpha$- or $\beta$-oriented; and pharmaceutically acceptable, non-toxic salts or easily hydrolyzable esters thereof and an inert carrier therefor.

* * * * *